(12) United States Patent
Hope Simpson et al.

(10) Patent No.: US 11,647,989 B2
(45) Date of Patent: May 16, 2023

(54) DEVICES, SYSTEMS, AND METHODS FOR MULTIMODAL ULTRASOUND IMAGING

(71) Applicant: KONINKLIJKE PHILIPS N.V., Eindhoven (NL)

(72) Inventors: David Hope Simpson, Bothell, WA (US); Andrew Hancock, Sacramento, CA (US); Jun Seob Shin, Medford, MA (US); Seungsoo Kim, Andover, MA (US); Jean-luc Francois-Marie Robert, Cambridge, MA (US); Francois Guy Gerard Marie Vignon, Andover, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 485 days.

(21) Appl. No.: 16/566,398

(22) Filed: Sep. 10, 2019

(65) Prior Publication Data

US 2020/0077985 A1 Mar. 12, 2020

Related U.S. Application Data

(60) Provisional application No. 62/729,562, filed on Sep. 11, 2018.

(51) Int. Cl.
*A61B 8/06* (2006.01)
*G01S 15/89* (2006.01)
(Continued)

(52) U.S. Cl.
CPC .............. *A61B 8/5207* (2013.01); *A61B 8/06* (2013.01); *A61B 8/12* (2013.01); *A61B 8/445* (2013.01);
(Continued)

(58) Field of Classification Search
CPC ........... A61B 8/5207; A61B 8/12; A61B 8/54; A61B 8/4494; A61B 8/56; A61B 8/06;
(Continued)

(56) References Cited

U.S. PATENT DOCUMENTS

| 6,213,947 | B1 | 4/2001 | Phillips |
| 6,450,959 | B1 | 9/2002 | Mo |

(Continued)

*Primary Examiner* — Colin T. Sakamoto

(57) ABSTRACT

Improved ultrasound imaging devices and methods of using the devices are provided. An intraluminal imaging device is configured process imaging data obtained using a single imaging sequence in different processing paths to generate B-mode and flow images. For example, an ultrasound imaging system includes an ultrasound imaging device comprising an array of acoustic elements and a processor in communication with the array. The processor activates the array of acoustic elements to acquire ultrasound data using a sequence of transmit-receive pairs, generates a B-mode image using the acquired ultrasound data, forms a plurality of sub-apertures comprising a portion of the transmit-receive pairs, groups the sub-apertures into temporally-spaced ensembles, determines a flow estimate based on a comparison of at least one of sub-apertures within an ensemble, ensembles within an aperture, or different apertures, and outputs a graphical representation of the B-mode image and the flow estimate to a display.

21 Claims, 9 Drawing Sheets

(51) Int. Cl.
  *G01S 7/52* (2006.01)
  *A61B 8/08* (2006.01)
  *A61B 8/12* (2006.01)
  *A61B 8/00* (2006.01)

(52) U.S. Cl.
  CPC .............. *A61B 8/4494* (2013.01); *A61B 8/54* (2013.01); *A61B 8/56* (2013.01); *G01S 7/52079* (2013.01); *G01S 7/52085* (2013.01); *G01S 15/8922* (2013.01); *G01S 15/8927* (2013.01); *G01S 15/8979* (2013.01); *A61B 8/4488* (2013.01); *A61B 8/5246* (2013.01)

(58) Field of Classification Search
  CPC ..... A61B 8/445; A61B 8/0891; A61B 8/0883; A61B 8/4488; A61B 8/5246; A61B 8/14; G01S 15/8979; G01S 15/8922; G01S 15/8927; G01S 7/52085; G01S 7/52079
  See application file for complete search history.

(56) References Cited

U.S. PATENT DOCUMENTS

| | | | |
|---|---|---|---|
| 6,679,847 | B1 | 1/2004 | Robinson |
| 9,360,552 | B2* | 6/2016 | Bae .................... G01S 7/52085 |
| 9,610,061 | B2* | 4/2017 | Ebbini .................... A61B 8/06 |
| 2005/0043622 | A1* | 2/2005 | Jensen ................ G01S 15/8915 |
| | | | 600/407 |
| 2007/0073153 | A1* | 3/2007 | Tortoli .................... A61B 8/06 |
| | | | 600/454 |
| 2007/0161904 | A1* | 7/2007 | Urbano ................ A61B 8/4438 |
| | | | 600/459 |
| 2008/0114239 | A1* | 5/2008 | Randall ................ G01S 7/5208 |
| | | | 600/437 |
| 2009/0326379 | A1* | 12/2009 | Daigle .................... A61B 8/06 |
| | | | 600/453 |
| 2013/0096433 | A1* | 4/2013 | Lemmerhirt ....... A61B 5/02007 |
| | | | 600/441 |
| 2013/0150719 | A1* | 6/2013 | Orderud ................ A61B 8/483 |
| | | | 600/443 |
| 2013/0303907 | A1 | 11/2013 | Corl |
| 2014/0018690 | A1 | 1/2014 | Guracar |
| 2014/0056099 | A1* | 2/2014 | Hancock .................. A61B 8/12 |
| | | | 367/11 |
| 2015/0087986 | A1 | 3/2015 | Nair |
| 2016/0007947 | A1* | 1/2016 | Spencer ................ A61B 8/0841 |
| | | | 600/424 |
| 2016/0051233 | A1 | 2/2016 | Mo |
| 2016/0089117 | A1 | 3/2016 | Kim |
| 2016/0157828 | A1* | 6/2016 | Sumi ...................... G01N 29/46 |
| | | | 702/189 |
| 2018/0088220 | A1* | 3/2018 | Flynn .................. G01S 15/8979 |
| 2019/0129026 | A1* | 5/2019 | Sumi .................. G01S 15/8915 |

* cited by examiner

FIG. 5

DEVICES, SYSTEMS, AND METHODS FOR MULTIMODAL ULTRASOUND IMAGING

TECHNICAL FIELD

The present disclosure relates generally to medical imaging and, in particular, to ultrasonic medical imaging devices configured to generate B-mode and flow images. For example, an ultrasonic medical imaging device can include an array of acoustic elements in communication with a processor configured to activate the array of acoustic elements according to a pulse sequence.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual acoustic elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

In IVUS imaging, a common clinical goal is distinguishing a vessel wall from the vessel lumen and surrounding tissue (i.e., vessel wall segmentation). Conventional IVUS systems rely on redundant multi-modal imaging methods that interleave ultrasound data from two separate imaging sequences, which can result in reduced frame rates.

SUMMARY

Embodiments of the present disclosure provide improved ultrasound imaging devices and methods of operating the devices that overcome the limitations described above. For example, an intraluminal imaging device is configured to perform a single imaging sequence to obtain ultrasound imaging data that is processed in different processing paths to generate B-mode and flow image data. In one embodiment, the imaging sequence comprises a plurality of apertures. Each aperture comprises a plurality of ensembles of sub-apertures. The sub-apertures comprise a plurality of transmit-receive pairs of ultrasound transducer elements arranged such that the transmit-receive pairs of one or more ensembles can be compared and/or combined to form a flow estimate for a flow image, and the same transmit-receive pairs of each aperture can be combined in a separate processing path to form an A-line for a B-mode image. Accordingly, the ensemble and sub-aperture arrangement of the imaging sequence can facilitate multimodal imaging without reducing the frame rate.

According to one embodiment, an ultrasound imaging system includes an ultrasound imaging device comprising an array of acoustic elements, and a processor in communication with the ultrasound imaging device. The processor is configured to acquire ultrasound data representative of an anatomy of a patient by activating a first plurality of acoustic elements in the array to transmit ultrasound signals and a second plurality of acoustic elements in the array to receive ultrasound echoes associated with the transmitted ultrasound signals, thereby forming a plurality of transmit-receive pairs of acoustic elements. The processor is further configured to form a plurality of sub-apertures from the acquired ultrasound data, each sub-aperture comprising a portion of the plurality of transmit-receive pairs, form a plurality of temporally-spaced ensembles by grouping the plurality of sub-apertures, determine a flow estimate associated with the anatomy based on at least one of a comparison of different sub-apertures within an ensemble, a comparison of different ensembles within an aperture, or a comparison of different apertures, generate a B-mode image using the acquired ultrasound data, and output, to a display in communication with the processor, a graphical representation of the B-mode image and the flow estimate.

In some embodiments, the ultrasound imaging device comprises an intravascular ultrasound (IVUS) imaging catheter. In some embodiments, the plurality of sub-apertures comprises non-contiguous sequences of the plurality of transmit-receive pairs. In other embodiments, the plurality of sub-apertures comprises contiguous sequences of the plurality of transmit-receive pairs. The processor is configured to generate a B-mode image stream and a flow image stream of the anatomy temporally corresponding to one another, in some embodiments. Each of the B-mode image stream and the flow image stream can comprise a frame rate of at least 30 Hz. In some aspects, the processor is configured to activate a first ensemble and a second ensemble to obtain a first ultrasound data set and a second ultrasound data set during a same pulse sequence. In some embodiments, each sub-aperture of the plurality of sub-apertures comprises between 4 and 8 transmit-receive pairs of acoustic elements. In some embodiments, each ensemble of the plurality of ensembles comprises between 2 and 6 sub-apertures.

In some aspects, the processor determining the flow estimate comprises: generating a first flow estimate from a first ensemble, and generating a second flow estimate from a second ensemble. The processor generating the B-mode image can include generating an A-line using transmit-receive pairs associated with the first and second ensembles. In another aspect, the processor determining the flow estimate comprises combining incoherently and averaging ultrasound data obtained by at least a portion of the plurality of ensembles to generate a flow A-line.

According to another embodiment, an ultrasound imaging method includes acquiring, by a processor in communication with an ultrasound imaging device, ultrasound data representative of an anatomy of a patient. The ultrasound imaging device includes an array of acoustic elements. Acquiring the ultrasound data includes activating a first plurality of acoustic elements in the array to transmit ultrasound signals and a second plurality of acoustic elements in the array to receive ultrasound echoes associated with the transmitted ultrasound signals, thereby forming a plurality of transmit-receive pairs of acoustic elements. The method further includes forming a plurality of sub-apertures from the acquired ultrasound data, each sub-aperture comprising a portion of the plurality of transmit and receive pairs, forming a plurality of temporally-spaced ensembles by grouping the plurality of sub-apertures, forming a plurality of apertures from the acquired ultrasound data, each aperture comprising a portion of the plurality of ensembles, determining a flow estimate associated with the anatomy based on at least one of a comparison of different sub-apertures within an ensemble, a comparison of different ensembles within an aperture, or a comparison of different apertures, generating a B-mode image using the acquired ultrasound data, and outputting, to a display in communication with the processor, a graphical representation of the B-mode image and the flow estimate.

In some embodiments, acquiring the ultrasound data comprises controlling an intravascular ultrasound (IVUS) imaging catheter positioned within a blood vessel of the patient. In some embodiments, forming the plurality of sub-apertures comprises activating non-contiguous sequences of the plurality of transmit-receive pairs. In other embodiments, forming the plurality of sub-apertures comprises activating contiguous sequences of the plurality of transmit-receive pairs. In one aspect, the method further includes generating, by the processor, a B-mode image stream and a flow image stream of a vessel of the patient temporally corresponding to one another, wherein each of the B-mode image stream and the flow image stream comprises a frame rate of at least 30 Hz. In another aspect, acquiring the ultrasound data includes activating, by the processor, a first ensemble to acquire a first ultrasound data set and activating, by the processor, a second ensemble to acquire a second ultrasound data set. Activating the first and second ensembles can include controlling, by the processor, the first and second ensembles to obtain the first ultrasound data set and second ultrasound data set during a same pulse sequence of the array of acoustic elements.

In some embodiments, each sub-aperture of the plurality of sub-apertures comprises between 4 and 8 transmit-receive pairs of acoustic elements. In some embodiments, each ensemble of the plurality of ensembles comprises between 2 and 6 sub-apertures. In one aspect, determining the flow estimate comprises generating a first flow estimate from a first ensemble, and generating a second flow estimate from a second ensemble. Generating the B-mode image can include generating an A-line using transmit-receive pairs associated with the first and second ensembles. In another aspect, the method further includes combining incoherently and averaging ultrasound data obtained by at least a portion of the plurality of ensembles to generate a flow A-line.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 5 is a diagrammatic graphical view of an ultrasound pulse sequence, according to aspects of the present disclosure.

DETAILED DESCRIPTION

Figure 1:
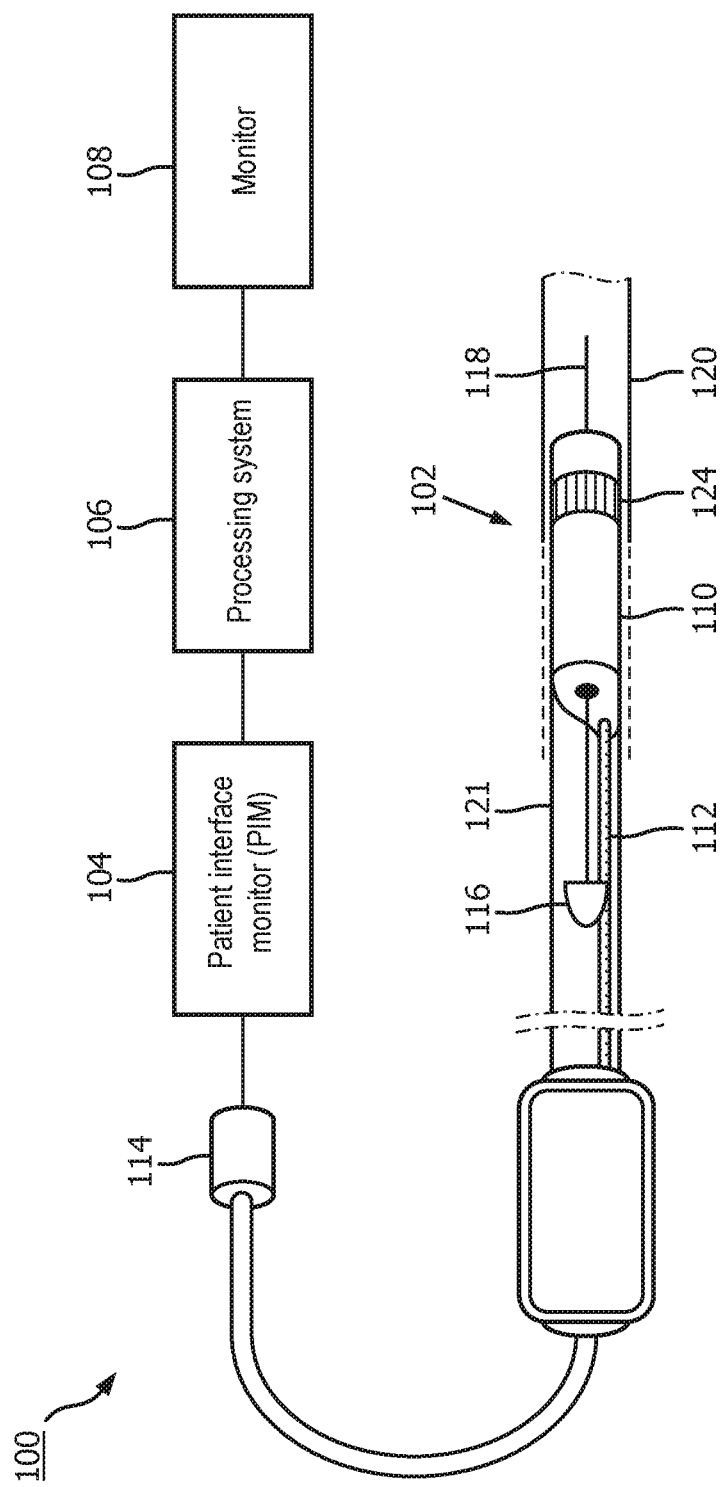
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100, according to aspects of the present disclosure. The intraluminal imaging system 100 can be an ultrasound imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be IVUS imaging device, such as a solid-state IVUS device.

At a high level, the IVUS device 102 emits ultrasonic energy, or ultrasound signals, from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
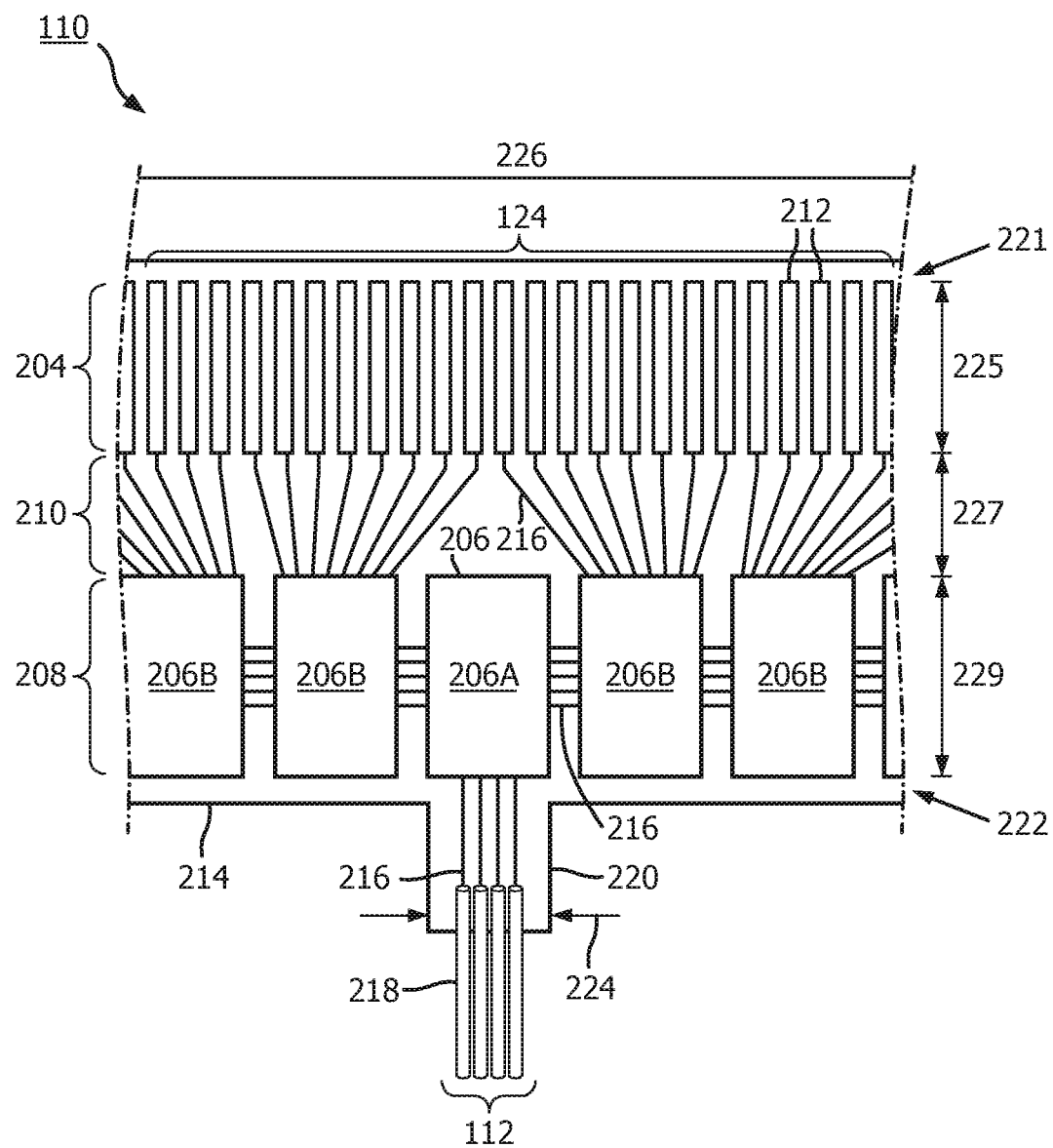
FIG. 2 is a diagrammatic perspective view of the top of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In an embodiment, the image processing system 106 generates flow data by processing the echo signals from the IVUS device 102 into Doppler power or velocity information. The image processing system 106 may also generate B-mode data by applying envelope detection and logarithmic compression on the conditioned echo signals. The processing system 106 can further generate images in various views, such as 2D and/or 3D views, based on the flow data or the B-mode data. The processing system 106 can also perform various analyses and/or assessments. For example, the processing system 106 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the processing system 106 can apply a blood flow detection algorithm (e.g., ChromaFlo) to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 106 may control to the device 102 to transmit repeated pulses on the same aperture.

While the present disclosure refers to intravascular ultrasound (IVUS) imaging using an intravascular catheter or guidewire, it is understood that one or more aspects of the present disclosure can be implemented in any synthetic aperture ultrasound imaging system. For example, aspects of the present disclosure can be implemented in intraluminal ultrasound imaging systems using an intracardiac (ICE)

echocardiography catheter and/or a transesophageal echocardiography (TEE) probe, and/or external ultrasound imaging system using an ultrasound probe configured for imaging while positioned adjacent to and/or in contact with the patient's skin.

FIG. 2 is a diagrammatic top view of a portion of a flexible assembly 200, according to aspects of the present disclosure. The flexible assembly 200 includes a transducer array 124 formed in a transducer region 204 and transducer control logic dies 206 (including dies 206A and 206B) formed in a control region 208, with a transition region 210 disposed therebetween. The transducer array 124 includes an array of ultrasound transducers 212. The transducer control logic dies 206 are mounted on a flexible substrate 214 into which the transducers 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 µm and 100 µm, with some particular embodiments being between 5 µm and 25.1 µm, e.g., 6 µm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 142 which may serve as an electrical conductor, e.g., electrical conductor 112, between a processing system, e.g., processing system 106, and the flexible assembly 200. Accordingly, the master control circuit may include control logic that decodes control signals received over the cable 142, transmits control responses over the cable 142, amplifies echo signals, and/or transmits the echo signals over the cable 142. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed in the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 142 when the conductors 218 of the cable 142 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 µm. For example, in an embodiment, 5 µm conductive traces 216 are separated by 5 µm of space. The width of a conductive trace 216 on the flexible substrate may be further determined by the width of the conductor 218 to be coupled to the trace/pad.

The flexible substrate 214 can include a conductor interface 220 in some embodiments. The conductor interface 220 can be a location of the flexible substrate 214 where the conductors 218 of the cable 142 are coupled to the flexible substrate 214. For example, the bare conductors of the cable 142 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
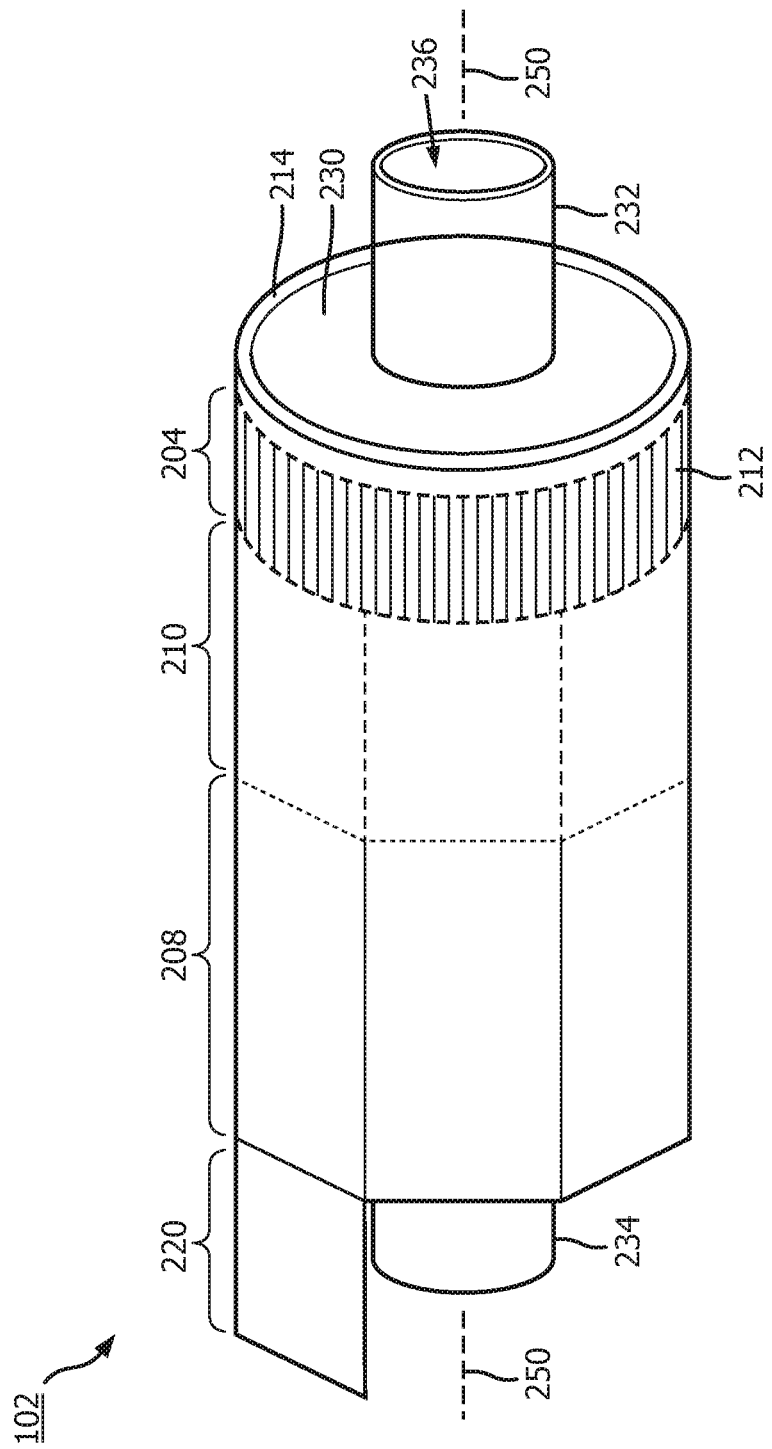
FIG. 3 is a diagrammatic perspective view of the scanner assembly shown in FIG. 2 in a rolled configuration around a support member, according to aspects of the present disclosure.

FIG. 3 illustrates a perspective view of the device 102 with the scanner assembly 110 in a rolled configuration. In some instances, the assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

In some embodiments, the transducer elements 212 and/or the controllers 206 can be positioned in an annular configuration, such as a circular configuration or in a polygon configuration, around a longitudinal axis 250 of a support member 230. It will be understood that the longitudinal axis 250 of the support member 230 may also be referred to as the longitudinal axis of the scanner assembly 110, the flexible elongate member 121, and/or the device 102. For example, a cross-sectional profile of the imaging assembly 110 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 application) the entirety of which is hereby incorporated by reference herein. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process.

Figure 4:
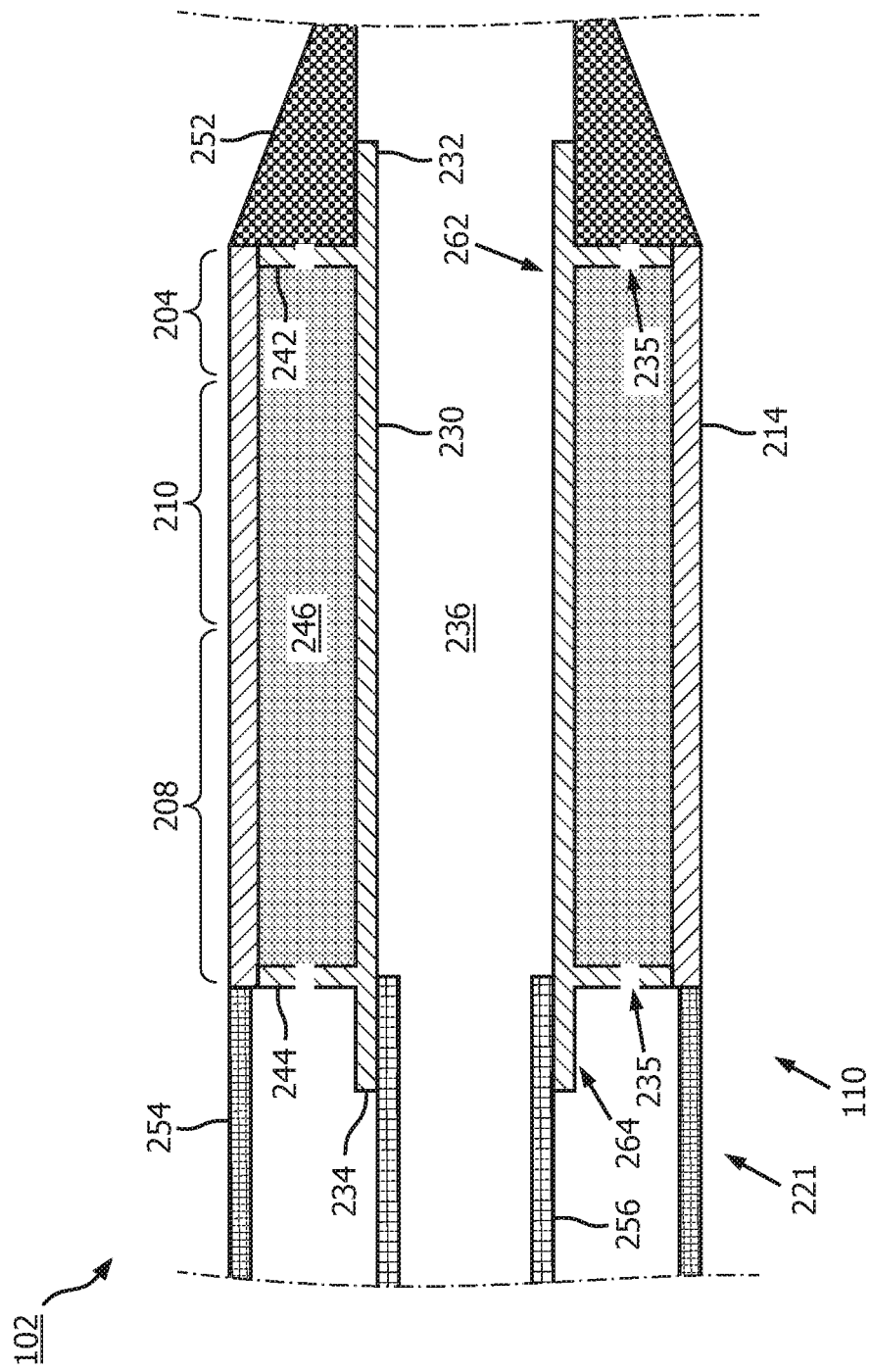
FIG. 4 is a diagrammatic cross-sectional side view of a scanner assembly in a rolled configuration around a support member, according to aspects of the present disclosure.

Referring now to FIG. 4, shown there is a diagrammatic cross-sectional side view of a distal portion of the intraluminal imaging device 102, including the flexible substrate 214 and the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985, 220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1). The support member 230 can be manufactured according to any suitable process. For example, the support member 230 can be machined and/or electrochemically machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion 204 (or transducer region 204), can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the proximal inner member 256, and/or the proximal outer member 254 can be coupled to one another via an adhesive.

To obtain a cross-sectional view of a patient's anatomy, such as a blood vessel, the array 124 of elements 212 is operated according to an ultrasound pulse sequence. The ultrasound pulse sequence includes instructions for activating individual elements of the array 124 to transmit ultrasound energy and/or receive ultrasound echoes from the patient's anatomy. Some ultrasound imaging systems may activate only one ultrasound transducer element at a time to transmit ultrasound energy and/or receive ultrasound echoes. Thus, an ultrasound pulse sequence may involve activating, in succession, a plurality of ultrasound transducer elements according to a predetermined pattern to form a single A-line of a B-mode image. In that regard, FIGS. 5-9 illustrate ultrasound pulse sequences of solid-state IVUS imaging systems where only one ultrasound transducer element is activated at a time to transmit ultrasound energy or receive ultrasound echoes.

Figure 5:
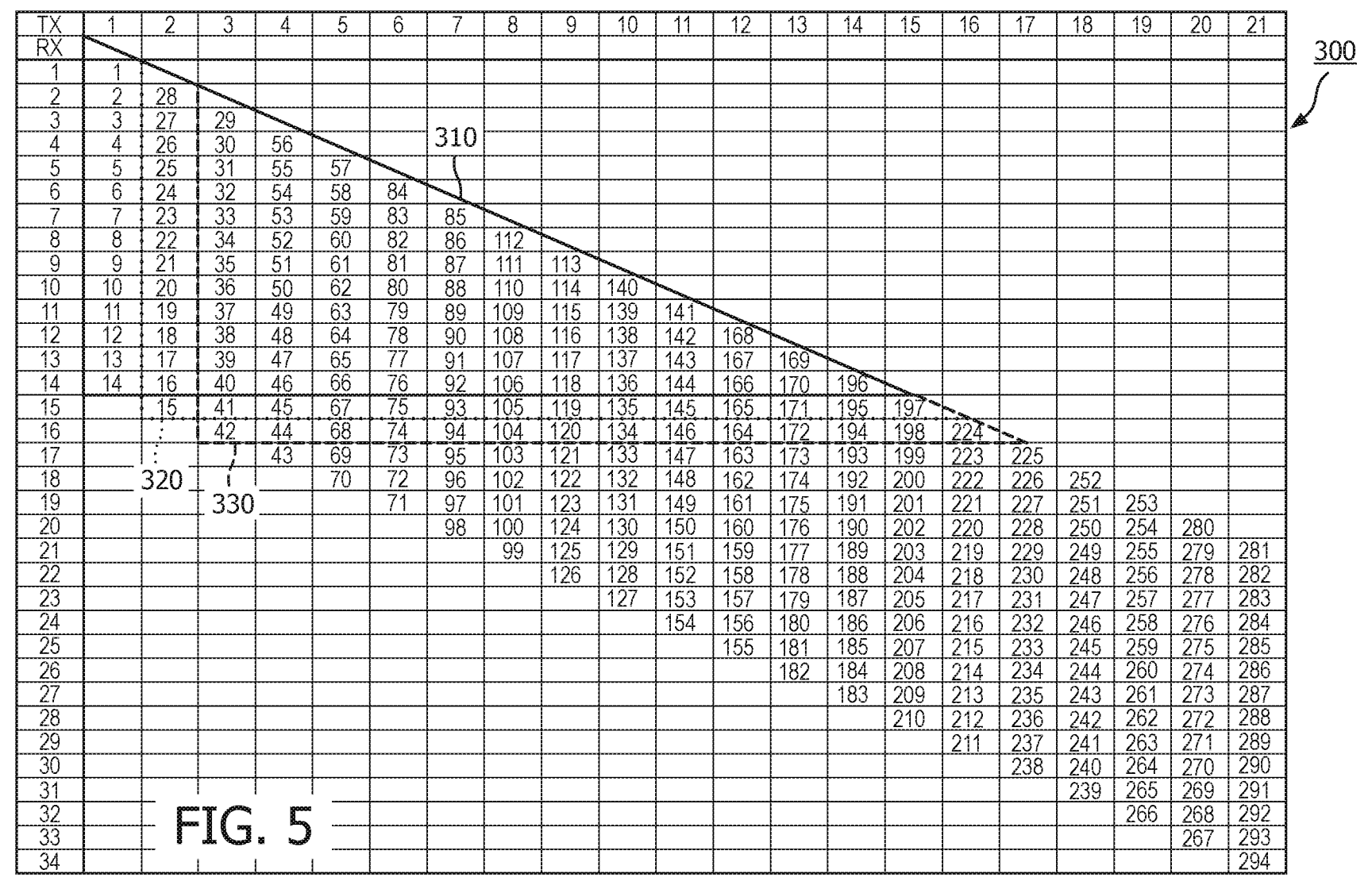

FIG. 5 is a diagrammatic graphical view showing an ultrasound pulse sequence of a solid-state IVUS device. The pulse sequence 300 comprises a contiguous "zig-zag" pattern or arrangement of transmit-receive pairs, which can alternatively be described as transmit-receive events. Each transmit-receive pair is represented by an index, or number, corresponding to a sequential time at which the corresponding transmit-receive pair is activated to obtain ultrasound imaging data. In that regard, each transmit-receive index is an integer representing its relative temporal position in the sequence 300. In the embodiment of FIG. 5, each transmit-receive index corresponds to a single transmit-receive pair. Each transmit-receive pair is defined by a transmit element index, shown on the x-axis, and a receive element index, shown on the y-axis. Each transmit element index and receive element index corresponds to an ultrasound element of an array of ultrasound transducer elements. In the embodiment shown in FIG. 5, the array comprises 64 ultrasound transducer elements.

For example, the transmit-receive pair associated with transmit-receive index "1" is defined by transmit element index number 1, and receive element index 1. In some embodiments, the transmit element index and receive element index correspond to the same ultrasound transducer element. In other embodiments, the transmit element index and receive element index correspond to different ultrasound transducer elements. For example, the transmit-receive pair numbered "2," which is shown directly below transmit-receive pair 1, is defined by transmit element index 1 and receive element index 2. That is, the ultrasound imaging data associated with transmit-receive pair 2 is obtained by activating transmit element index 1 to transmit ultrasound energy into the patient volume, and then activating receive element index 2 to receive ultrasound echoes from the patient volume. In FIG. 5, 294 transmit-receive pairs of an ultrasound pulse sequence are shown. Each transmit-receive pair is activated sequentially according to its transmit-receive index.

In the sequence 300, the ultrasound transducer element associated with transmit index 1 transmits 14 consecutive times, while the elements associated with receive indices 1 through 14 are sequentially activated to receive the corresponding echoes. Next, the element associated with transmit index 2 transmits 14 consecutive times, while the elements associated with receive indices 15 through 2 (stepping backward) are sequentially activated to receive the corresponding echoes. This sequence continues in a zig-zag pattern around the array of ultrasound transducer elements. Each transmit-receive pair is associated with one or more apertures 310, 320, 330. For example, a first aperture 310 comprises transmit-receive pairs spanning from index 1 to index 196, a second aperture 320 comprises transmit-receive pairs spanning from index 15 to index 197, and a third aperture 330 comprises transmit-receive pairs spanning from index 29 to index 224. The transmit-receive pairs in each aperture are combined to form an A-line for a B-mode image. Thus, the transmit-receive pairs contained within the first aperture 310 are combined to form a first A-line, the transmit-receive pairs contained within the second aperture 320 are combined to form a second A-line, the transmit-receive pairs contained within the third aperture are combined to form a third A-line, and so on. The A-line formed by the first aperture 310 will be centered between transmit and receive element indices 7 and 8, the A-line formed by the second aperture 320 will be centered between transmit and receive element indices numbered 8 and 9, the A-line formed by the third aperture 330 will be centered between transmit and receive element indices numbered 9 and 10, and so on. Several apertures are used to form A-lines, which are combined and arranged to form a B-mode image.

It will be understood that, to complete the sequence 300 shown in FIG. 5 for an ultrasound transducer array comprising 64 elements, 64 apertures comprising a total of 896 transmit-receive pairs are used to form a single B-mode image frame. However, if pulse averaging is used to increase signal-to-noise ratio, at least twice as many transmit-receive pairs (1792) are required. At a pulse repetition frequency of 50 kHz, 1792 transmit-receive pairs corresponds to a 30 Hz frame rate, which is near the minimum acceptable frame rate for real-time imaging, and may already limit the ability to do pullbacks with an IVUS imaging device.

When a physician desires to view flow images in addition to the B-mode images, conventional pulse sequences may require additional dedicated pulse sequences to obtain flow data, where the additional dedicated pulse sequences are interleaved with the B-mode image data. However, due to the already constrained frame rates provided by conventional pulse sequences, interleaving additional dedicated flow pulse sequences may be undesirable for providing a live image stream with adequate temporal resolution.

Accordingly, it is desirable to provide a multimodal pulse sequence that provides B-mode image data and flow data without adding dedicated flow pulse sequences. One solution is to use smaller subsets of transmit-receive pairs, such as sub-apertures, to form flow A-lines, and to use the same transmit-receive pairs to form A-lines for a B-mode image.

Since the sub-apertures are formed at different times, it is possible to detect motion between acquisition of the sub-apertures.

In order to facilitate the multimodal functionality of the pulse sequence, a number of design factors are relevant. First, sub-apertures are compared that share the same k-space in order to avoid bias in the change detection due to discrepancy in point spread functions (psf). K-spaces in synthetic aperture ultrasound are described, for example, in Hoctor and Kassam, "The unifying role of the co-array in aperture synthesis for coherent and incoherent imaging", Proceedings of the IEEE, Vol. 78, No 4, April 1990, the entirety of which is hereby incorporated by reference. Only transmit-receive pairs that satisfy the relationship: tx+rx=constant are compared. Transmit-receive pairs combined into sub-apertures should be temporally close to each other in order to avoid blood low-pass filtering within a sub-aperture. This may constrain the maximum size of a sub-aperture that is used. Sub-apertures compared to one another are equally spaced temporally, in order to use conventional Doppler estimators. This factor can be relaxed or ignored with the use of more advanced estimators and a knowledge of time intervals between sub-aperture acquisitions. Sub-apertures should be large enough (e.g., 2 or more elements across) for acceptable SNR and resolution. Sixth, dwell times should be long enough to allow for adequate detection of blood flow. Wall filters may not be necessary; thus, Nyquist sampling is not used in some embodiments. Ensemble lengths, that is, the number of sub-apertures within an ensemble, should be long enough to achieve an acceptable SNR.

Figure 6:
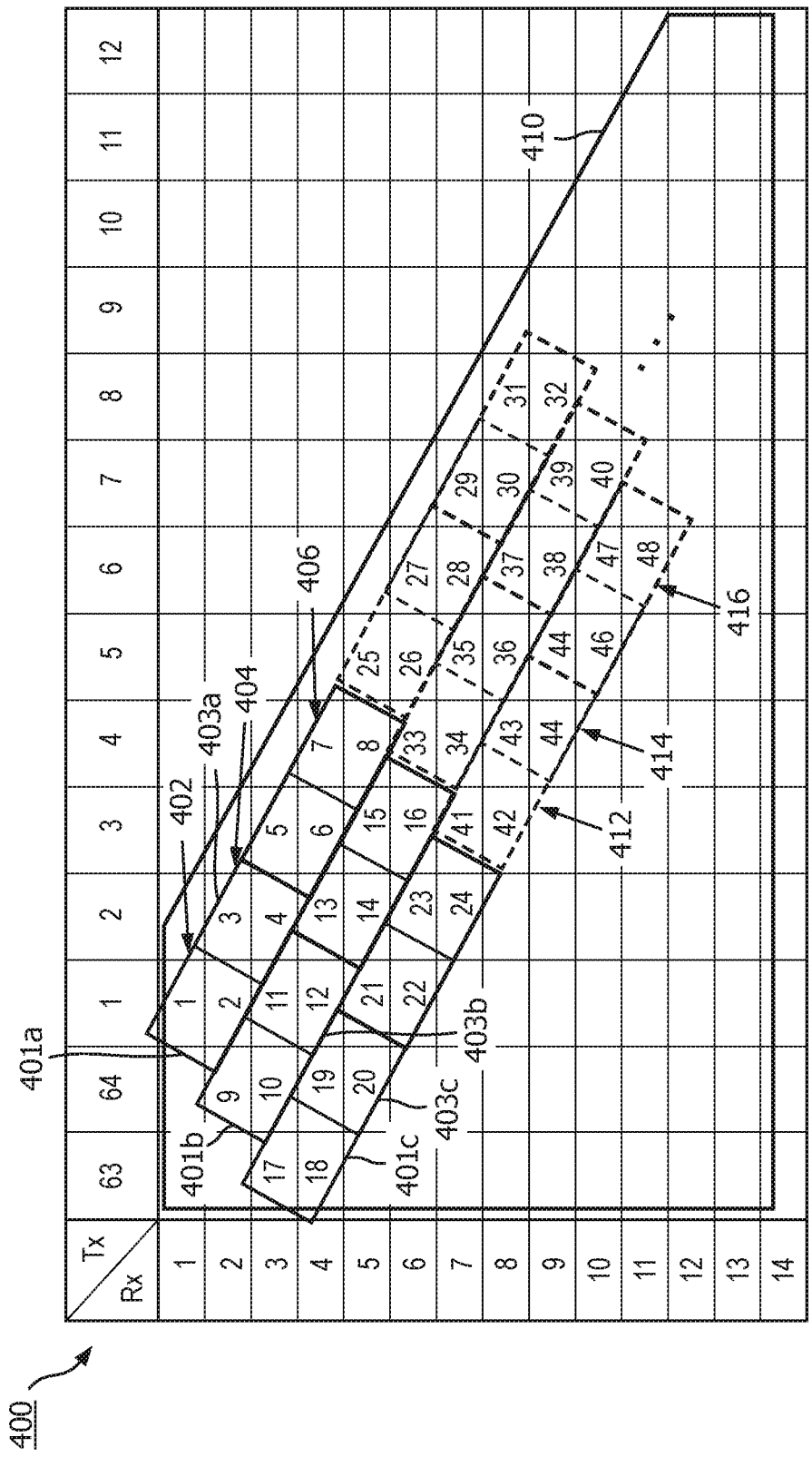
FIG. 6 is a diagrammatic graphical view of a multimodal ultrasound pulse sequence, according to aspects of the present disclosure.

FIG. 6 is a diagrammatic graphical view showing an ultrasound pulse sequence 400 of a solid state IVUS device, according to some embodiments of the present disclosure. The pulse sequence 400 comprises multiple ensembles 402, 404, 406, 412, 414, 416. Each ensemble comprises a plurality of sub-apertures, with each sub-aperture represented by a rectangular box encompassing four indexed transmit-receive pairs, or transmit-receive events. In other words, each transmit-receive pair is associated with a sub-aperture, and each sub-aperture is associated with an ensemble. The transmit-receive pairs also form an aperture 410, which defines the number of transmit-receive pairs used to form a single A-line of a B-mode image. Several apertures of a pulse sequence are used to form A-lines that are combined and arranged to form a B-mode image.

A plurality of apertures of an ultrasound imaging sequence can define a field of view of an ultrasound imaging device. Thus, each individual aperture can define a portion or segment of the field of view. For example, for an IVUS device wherein the acoustic elements of the array are disposed around a circumference of the device, the field of view may be circular and centered around a longitudinal axis of the device. Each aperture is associated with a single line or angular portion (e.g., slice) of the circular field of view. In an external ultrasound probe having a substantially straight array of acoustic elements, each aperture is associated with a single line or rectangular portion of a substantially rectangular field of view.

In this example, each ensemble comprises three sub-apertures corresponding to a similar k-space. For instance, ensemble 402 comprises sub-apertures 401a, 401b, and 401c, while ensemble 404 comprises sub-apertures 403a, 403b, and 403c. In the embodiment of FIG. 6, neighboring ensembles, such as ensembles 402 and 404 overlap such that they share at least some transmit-receive elements. In that regard, sub-aperture 401a and sub-aperture 403a share transmit-receive pairs numbered 3 and 4; sub-aperture 401b and 403b share transmit-receive pairs numbered 11 and 12, etc.

Transmit-receive pairs within each sub-aperture can be combined through beamforming (e.g., delay and sum beamforming). The sub-apertures of each ensemble can combined to form a flow estimate. In that regard, because the sub-aperture of each ensemble comprise ultrasound imaging data obtained at different times, the sub-apertures can be compared/combined to detect motion of the patient volume (e.g., blood flowing through a blood vessel) between each sub-aperture. For example, the autocorrelation algorithm can be applied to measure the phase shift between sub-apertures within an ensemble, and that phase shaft can be converted into blood velocity. Other flow estimation techniques can be used, including techniques for clutter filtering and unaliased motion estimation. Any other suitable mathematical process can be used to compare and/or combine transmit-receive pairs, sub-apertures, and/or ensembles, such as averaging or subtraction.

In order to reliably extract flow or blood velocity information from the sequence 400, the arrangement of sub-apertures in each ensemble, as well as the arrangement of transmit-receive pairs in each sub-aperture, follows a set of guidelines. For example, the sub-apertures compared in each ensemble share the same k-space in order to avoid bias in the change detection due to discrepancies in point spread functions. Thus, transmit-receive pairs that satisfy the relationship: tx+rx=constant are compared. Furthermore, transmit-receive pairs combined within a sub-aperture are temporally close (i.e., sequential indices are close) to each other in order to avoid blood low-pass filtering within a sub-aperture. Sub-apertures compared in each ensemble are ideally equally spaced temporally in the sequence such that conventional Doppler estimators can be used, although this configuration can be modified or relaxed if the relative timing between sub-apertures is known, and with the use of more advanced motion estimators than the conventional autocorrelation algorithm, for example, cross-correlation. This configuration can also be modified or relaxed if only blood detection (e.g., movement) is desired, as opposed to blood velocity estimation. Sub-apertures should include enough transmit-receive pairs to achieve an acceptable signal-to-noise (SNR) and resolution of the flow image. For example, each sub-aperture includes transmit-receive pairs spanning at least two ultrasound transducer elements across.

In the embodiment of FIG. 6, each ensemble (e.g., 402, 404, etc.) in the sequence 400 has a length of three. That is, each ensemble comprises three sub-apertures. The sequence 400 has a sampling interval of 8 pulse repetition intervals (PRIs). The PRI can be described as the time interval between successive transmit-receive events. The dwell time, which can be described as the time elapsed between the first and the last sub-apertures in an ensemble, is 16 PRI's. The sub-apertures in each ensemble are compared to create a Doppler sample. The Doppler samples from several consecutive ensembles (e.g., 402 to 416, or any other consecutive grouping therein) can be combined coherently or incoherently to form a flow estimate for a flow A-line. All transmit-receive pairs of the aperture 410 are coherently beamformed to create a single B-mode image A-line. In an exemplary embodiment, the aperture 410 spans 14 elements in both the transmit and receive directions. In other embodiments, the aperture 410 spans fewer or more elements, such as 10, 12, 15, 16, 20, or any suitable number of ultrasound transducer elements. In some embodiments, the flow estimates are obtained by comparing a plurality of different ensembles within an aperture. In other embodiments, flow estimates or flow A-lines are obtained by comparing flow estimates generated from comparing a plurality of different apertures. While a portion of only one aperture 410 is illustrated in FIG. 6, it is understood that other subsets of ensembles can form other apertures, which can be compared to the aperture 410 to form a flow estimate.

In some embodiments, the flow estimates formed from each ensemble or from subsets of adjacent ensembles are combined incoherently and averaged to form a single flow A-line corresponding to the B-mode image A-line. As explained above, the sequence 400 shown in FIG. 6 can facilitate generation of a flow A-line as well as a B-mode image A-line without the need for separate, dedicated scan sequences for a flow image and a B-mode image. Flow A-lines and B-mode A-lines can be combined from several apertures to form a flow image and a B-mode image. Therefore, the sequence 400 shown in FIG. 6 can use the same transmit-receive pairs of a sequence to generate a B-mode image and a temporally-corresponding flow image.

The image sequence 400 includes transitions, or "jumps," from one transmit and/or receive element to another transmit and/or receive element. For example, the jump from transmit-receive index 1 to transmit-receive index 2 does not change the transmission element, but jumps one receive element (receive element 1 to receive element 2). The jump from transmit-receive index 2 to transmit index 3 jumps from transmit element 1 to transmit element 2, but does not change the receive element. Later in the sequence, the jump from transmit-receive index 8 to transmit-receive index 9 requires a jump from transmit element 4 to transmit element 64, and a jump from receive element 5 to receive element 2. Some IVUS architectures, such as multiplexing or beamforming architectures, may not allow non-contiguous multi-element jumps, such as the jump from transmit-receive index 8 to transmit-receive index 9.

Figure 7:
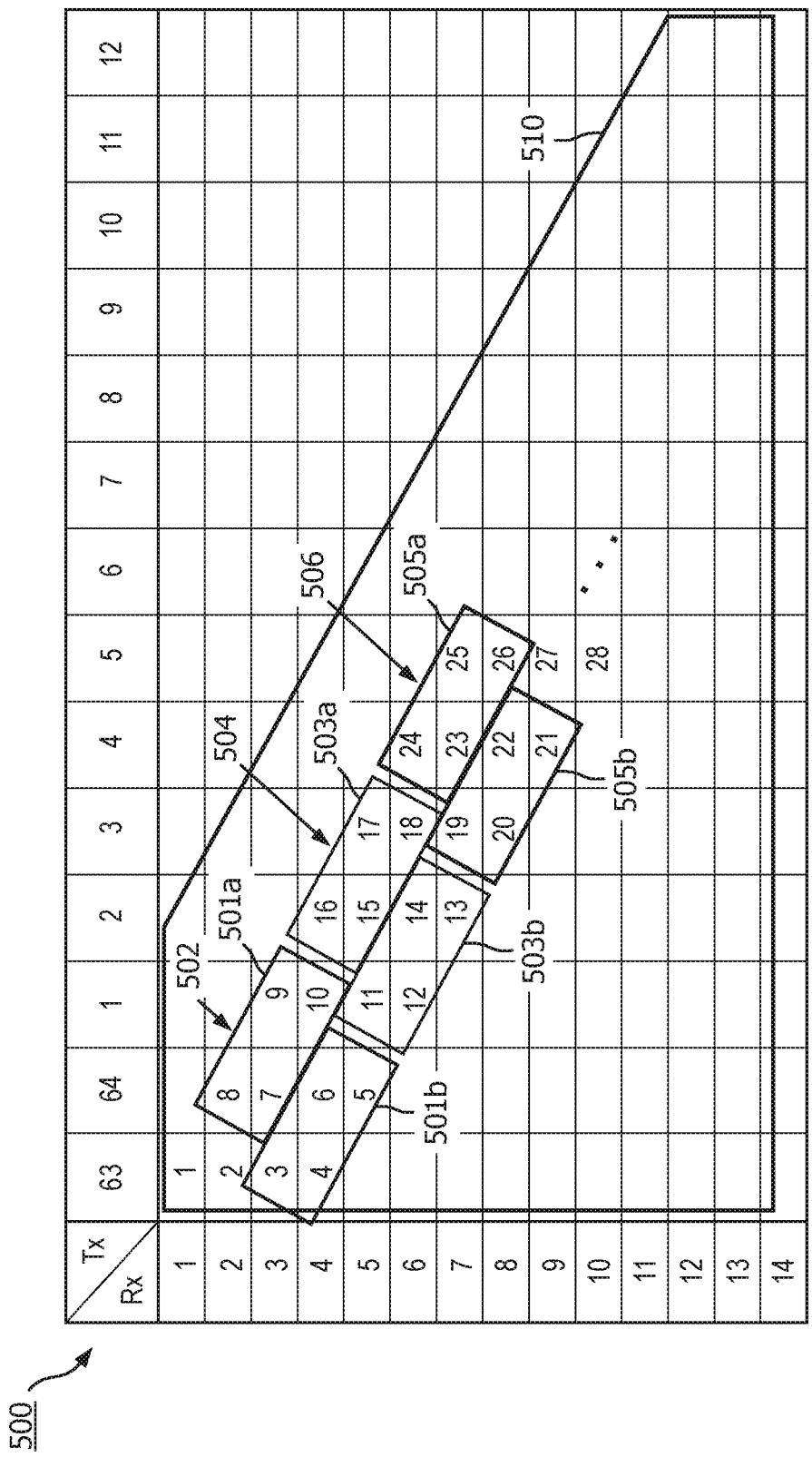
FIG. 7 is a diagrammatic graphical view of a multimodal ultrasound pulse sequence, according to aspects of the present disclosure.

FIG. 7 is a graphical view of an image sequence 500, according to another embodiment. In order to accommodate some conventional IVUS architectures, as explained above, the sequence 500 requires jumps of at most one transmit element and/or one receive element, in contrast to the sequence 400 shown in FIG. 6, which requires some non-contiguous jumps of as much as 4 transmit elements and 2 receive elements. In that regard, each of the jumps in the image sequence 500 can be described as contiguous, while the sequence 400 in FIG. 6 includes both contiguous and non-contiguous jumps.

Referring to FIG. 7, the sequence 500 of transmit-receive pairs is arranged in a zig-zag pattern, where each transmit element is used for four consecutive transmit-receive pairs, with the sequence cascading down the receive elements after each group of four consecutive transmit-receive pairs. Like the sequence 400 of FIG. 6, the sequence 500 shown in FIG. 7 includes a plurality of ensembles 502, 504, and 506, each of which includes a plurality of sub-apertures. For example, a first ensemble 502 comprises sub-apertures 501a and 501b, a second ensemble 504 comprises sub-apertures 503a and 503b, and a third ensemble 506 comprises sub-apertures 505a and 505b. The ensembles 502, 504, and 506 form part of an aperture 510, which can be used to generate a single A-line and/or flow estimate. Unlike the sequence of FIG. 6, the sub-apertures of each ensemble in FIG. 7 do not overlap. This may be in part due to the consecutive, zig-zag pattern of transmit-receive pairs, which creates greater temporal space between neighboring sub-apertures, which may be non-ideal for overlapping sub-apertures, as greater temporal spacing between transmit-receive pairs within a sub-aperture can result in undesirable low-pass filtering. However, in some embodiments, the zig-zag sequence 500 in FIG. 7 can be arranged into overlapping sub-apertures similar to those of FIG. 6.

The sequence 500 may provide many of the advantages of the sequence 400 explained above with respect to FIG. 6, but without requiring jumps of more than one transmit-receive element at a time. This may allow the sequence 500 to be implemented on existing systems having hardware that limits the amount and type of jumps between transmit-receive pairs of the sequence. Similar to the sequence 400 shown in FIG. 6, the sequence 500 in FIG. 7 may span approximately 14 transmit elements and 14 receive elements. In other embodiments, the sequence may span fewer or more transmit and/or receive elements.

Figure 8:
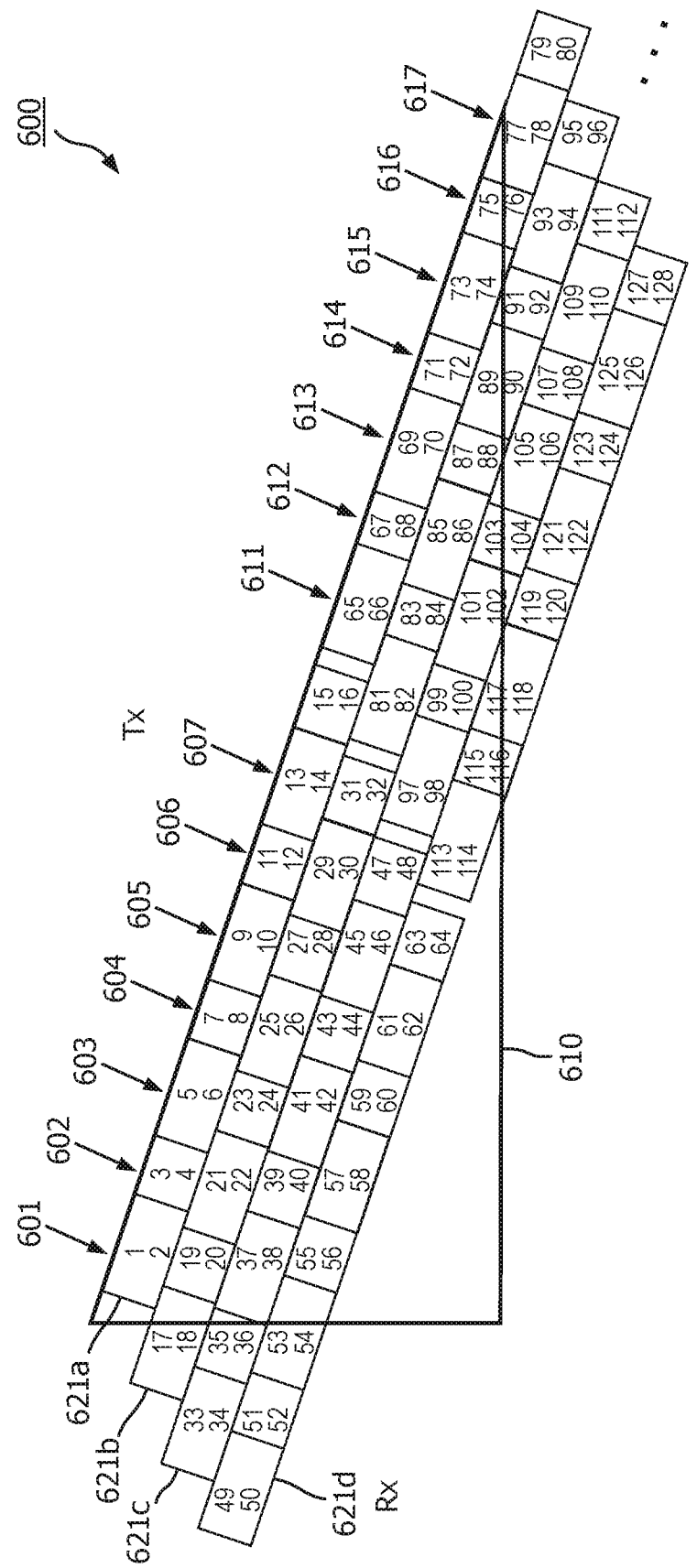
FIG. 8 is a diagrammatic graphical view of a multimodal ultrasound pulse sequence, according to aspects of the present disclosure.

FIG. 8 is a graphical view of an image sequence 600, according to another embodiment of the present disclosure. The sequence 600 may be similar to the sequence 400 shown in FIG. 6, in some aspects. For example, the sequence 600 shown in FIG. 8 comprises a plurality of ensembles, or pluralities of sub-apertures, where each ensemble comprises a plurality of sub-apertures. Each ensemble comprises four sub-apertures (i.e., ensemble length of four), and each sub-aperture comprises four transmit-receive pairs. For example, ensemble 601 comprises sub-apertures 621, 621b, 621c, and 621d. Like the sequence 400 in FIG. 6, the sequence 600 in FIG. 8 comprises a cascading pattern comprising a series of contiguous jumps, and a larger jump after each group of sixteen jumps. In that regard, the sequence 600 includes a jump between transmit-receive pair 16 and transmit-receive pair 17 that jumps from transmit element 8 to transmit element 64, and from receive element 9 to receive element 2. The ensembles form an aperture 610 spanning fourteen transmit elements and fourteen receive elements. As above, the sub-apertures in each ensemble are used to form one Doppler sample. The Doppler samples formed from several neighboring ensembles (e.g., 601 to 616), can be processed together to form a Doppler estimate, or a flow A-line. For example, in some embodiments, all Doppler estimates formed by sub-apertures within the aperture 610 are combined incoherently to reduce variance of the Doppler estimate to form a single flow A-line. To form the corresponding B-mode image, all transmit-receive pairs of the aperture 610 are combined.

Figure 9:
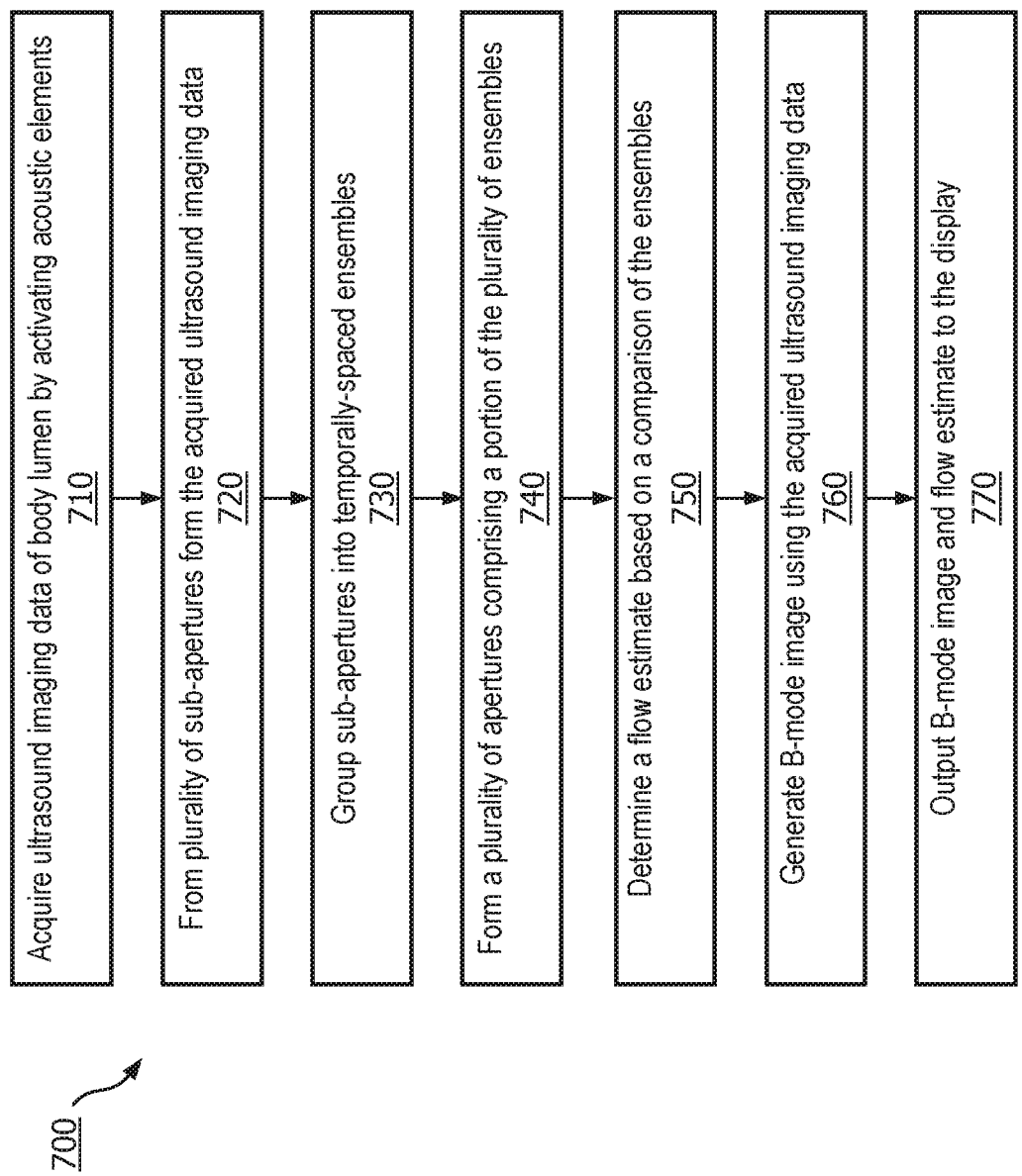
FIG. 9 is a flow diagram of a method for controlling an ultrasound imaging system to perform a multimodal ultrasound pulse sequence, according to aspects of the present disclosure.

A method 700 for multimodal ultrasound imaging is shown in FIG. 9. It will be understood that one or more steps of the method 700 can be performed using an ultrasound imaging system, such as the system 100 described above. In step 710, an ultrasound system acquires ultrasound imaging data of a body lumen of a vessel by activating a first plurality of acoustic elements in the array to transmit ultrasound signals, and a second plurality of acoustic elements in the array to receive ultrasound echoes associated with the transmitted ultrasound signals. The plurality of sub-apertures are activated by a processor according to a sequence of transmit-receive pairs of ultrasound transducer elements. In some embodiments, the ultrasound imaging data is acquired by controlling an intravascular ultrasound (IVUS) imaging catheter positioned within a blood vessel.

In step 720, the processor forms a plurality of temporally-spaced sub-apertures from the acquired ultrasound imaging data. As explained above, each sub-aperture may comprise a plurality of transmit-receive pairs. In some embodiments, each sub-aperture comprises between 4 and 8 transmit-receive pairs of acoustic elements. The transmit-receive pairs in each sub-aperture may be temporally close and/or spatially close together. The transmit-receive pairs of each sub-aperture may be arranged to share the same k-space. In an exemplary embodiment, each sub-aperture comprises a contiguous grouping of transmit-receive pairs of the sequence. However, the sequence may include one or more non-contiguous transmit-receive pairs. In that regard, forming the plurality of sub-apertures may include activating one or more non-contiguous sequences of transmit-receive pairs of acoustic elements. In other embodiments, forming the sub-apertures may include activating only contiguous sequences of transmit-receive pairs of acoustic elements. In step 730, the processor groups the plurality of sub-apertures into a plurality of temporally-spaced ensembles. In some embodiments, between 2 and 6 sub-apertures are grouped together to form each ensemble. The temporal spacing between sub-apertures in an ensemble may facilitate the detection of change resulting from movement in the image, such as blood flow, when the sub-apertures are compared and/or combined. For example, the processor may group sub-apertures into a first ensemble to define a first ultrasound data set, and group sub-apertures into a second ensemble to define a second ultrasound data set, wherein the first and second ensembles are formed from a same, non-interleaved pulse sequence of the array of acoustic elements.

In step 740, the processor forms a plurality of apertures of the pulse sequence by grouping together a plurality of transmit-receive pairs of the pulse sequence. In that regard, each aperture may comprise a plurality of ensembles and sub-apertures. Each aperture may be formed or defined by a number of acoustic elements. For example, in an exemplary embodiment, each aperture spans 14 acoustic elements. Similar to the overlapping of sub-apertures, in some embodiments, a single transmit-receive pair may be associated with a plurality of apertures. Similarly, a single sub-aperture or ensemble may also be associated with a plurality of apertures.

In step 750, a flow estimate, which, in some aspects, may also be referred to as a Doppler estimate or a velocity estimate, is determined by the processor by comparing and/or combining at least one of different sub-apertures within an ensemble, different ensembles within an aperture, and different apertures. For example, generating the flow estimate can include generating a Doppler sample by comparing and/or combining transmit-receive pairs of a single sub-aperture. Doppler samples associated with different sub-apertures of an ensemble can be processed together to form a Doppler estimate, or a flow estimate. In some embodiments, each flow estimate is used to generate a flow A-line. In other embodiments, several flow estimates from different ensembles are processed together (e.g., averaged) to generate a single flow A-line. In still other embodiments, flow estimates generated from different apertures are combined to form a single A-line. An A-line for a B-mode image can be generated by using ultrasound imaging data acquired by all transmit-receive pairs within an aperture.

In step 760, the processor generates a B-mode image using the acquired ultrasound imaging data. Generating the B-mode image can include combining and processing all transmit-receive pairs within an aperture to create a single A-line for the B-mode image. Thus, the B-mode image may be generated based on ultrasound imaging data acquired during the same pulse sequence used to form the plurality of sub-apertures and ensembles associated with the flow estimates described above. Thus, a separate pulse sequence need not be interleaved in order to generate B-mode image data and flow data.

A-lines generated from a plurality of apertures of the pulse sequence are combined and arranged to form the B-mode image. In some embodiments, the system is configured to generate a B-mode image stream to provide a live view of the vessel. In some embodiments, the B-mode image stream has a frame rate of at least 30 Hz.

In step 770, the processor outputs a B-mode image and the determined flow estimate to the display. For example, a graphical representation of the B-mode image and a flow-image may be output to the display and may comprise a flow-image overlaid on the B-mode image. In other embodiments, the flow-image and the B-mode image are displayed side-by-side on the display. In some embodiments, a combined B-mode/flow image which incorporates aspects of the B-mode image and the flow image is output to the display. In some embodiments, the system may allow a user to toggle on or off either the B-mode image or the flow image.

The method can facilitate the generation of both a flow image and a B-mode image using the same transmit-receive pairs of a single pulse sequence. Because dedicated flow imaging sequences and B-mode imaging sequences are not necessary, increased frame rates for combined flow/B-mode images can be achieved, as well as increased efficiency in operating the imaging system.

It will be understood that one or more of the steps of the method, such as activating the first and second pluralities of sub-apertures, generating the flow image and B-mode image, and outputting the graphical representation of the images to the display can be performed by one or more components of an ultrasound imaging system, such as the processor, a multiplexer, a beamformer, a signal processing unit, an image processing unit, or any other suitable component of the system. For example, activating the first and second pluralities of sub-apertures may be carried out by a processor in communication with a multiplexer configured to select or activate one or more elements of an ultrasound transducer array. In some embodiments, generating the flow image and B-mode image may include beamforming incoming signals from the ultrasound imaging device and processing the beamformed signals by an image processor. The processing components of the system can be integrated within the ultrasound imaging device, contained within an external console, or may be a separate component.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
an ultrasound imaging device comprising an array of acoustic elements; and
a processor in communication with the ultrasound imaging device and configured to:
acquire ultrasound data representative of an anatomy of a patient by activating a first plurality of acoustic elements in the array to transmit ultrasound signals and a second plurality of acoustic elements in the array to receive ultrasound echoes associated with the transmitted ultrasound signals according to a predetermined sequence, thereby forming a plurality of transmit-receive events;
form a plurality of event groupings, wherein each event grouping comprises a respective subset of the plurality of transmit-receive events;
form a plurality of temporally-spaced ensembles, wherein each ensemble comprises a respective subset of the plurality of event groupings;
determine a flow estimate associated with the anatomy based on at least one of:
a comparison of the ultrasound data associated with different event groupings within an ensemble; or
a comparison of the ultrasound data associated with different ensembles;
generate a B-mode image using the acquired ultrasound data; and
output, to a display in communication with the processor, a graphical representation of the B-mode image and the flow estimate.

2. The system of claim 1, wherein the ultrasound imaging device comprises an intravascular ultrasound (NUS) imaging catheter.

3. The system of claim 1, wherein the predetermined sequence comprises a non-contiguous ordering of the plurality of transmit-receive events.

4. The system of claim 1, wherein the predetermined sequence comprises a contiguous ordering of the plurality of transmit-receive events.

5. The system of claim 1, wherein the processor is configured to generate a B-mode image stream and a flow image stream of the anatomy temporally corresponding to one another, and wherein each of the B-mode image stream and the flow image stream comprises a frame rate of at least 30 Hz.

6. The system of claim 1, wherein the processor is configured to activate a first set of acoustic elements and a second set of acoustic elements to obtain a first ultrasound data set and a second ultrasound data set during a same pulse sequence.

7. The system of claim 1, wherein each event grouping of the plurality of event groupings comprises between 4 and 8 transmit-receive events.

8. The system of claim 7, wherein each ensemble of the plurality of ensembles comprises between 2 and 6 event groupings.

9. The system of claim 1,
wherein the processor determining the flow estimate comprises:
generating a first flow estimate from a first ensemble; and
generating a second flow estimate from a second ensemble, and
wherein the processor generating the B-mode image comprises generating an A-line using transmit-receive pairs associated with the first and second ensembles.

10. The system of claim 1, wherein the processor determining the flow estimate comprises combining incoherently and averaging ultrasound data obtained by at least a portion of the plurality of ensembles to generate a flow A-line.

11. The system of claim 1,
wherein the processor is configured to form a plurality of ensemble groupings, wherein each ensemble grouping comprises a respective subset of the plurality of ensembles, and
wherein the processor is configured to determine the flow estimate based on a comparison of the ultrasound data associated with different ensemble groupings.

12. An ultrasound imaging method, comprising:
acquiring, by a processor in communication with an ultrasound imaging device, ultrasound data representative of an anatomy of a patient, the ultrasound imaging device comprising an array of acoustic elements, wherein acquiring the ultrasound data includes activating a first plurality of acoustic elements in the array to transmit ultrasound signals and a second plurality of acoustic elements in the array to receive ultrasound echoes associated with the transmitted ultrasound signals according to a predetermined sequence, thereby forming a plurality of transmit-receive events;
forming a plurality of event groupings, wherein each event grouping comprises a respective subset of the plurality of transmit and receive events;
forming a plurality of temporally-spaced ensembles, wherein each ensemble comprises a respective subset of the plurality of event groupings;
determining a flow estimate associated with the anatomy based on at least one of:
a comparison of the ultrasound data associated with different event groupings within an ensemble; or
a comparison of the ultrasound data associated with different ensembles;
generating a B-mode image using the acquired ultrasound data; and
outputting, to a display in communication with the processor, a graphical representation of the B-mode image and the flow estimate.

13. The method of claim 12, wherein acquiring the ultrasound data comprises controlling an intravascular ultrasound (IVUS) imaging catheter positioned within a blood vessel of the patient.

14. The method of claim 12, wherein forming the plurality of event groupings comprises activating non-contiguous sequences of the plurality of transmit-receive pairs.

15. The method of claim 12, wherein forming the plurality of event groupings comprises activating contiguous sequences of the plurality of transmit-receive pairs.

16. The method of claim 12, further comprising generating, by the processor, a B-mode image stream and a flow image stream of a vessel of the patient temporally corresponding to one another, wherein each of the B-mode image stream and the flow image stream comprises a frame rate of at least 30 Hz.

17. The method of claim 12, wherein acquiring the ultrasound data comprises activating, by the processor, a first set of acoustic elements to acquire a first ultrasound data set and activating, by the processor, a second set of acoustic elements to acquire a second ultrasound data set, wherein activating the first and second sets of acoustic elements comprises controlling, by the processor, the first and second sets of acoustic elements to obtain the first ultrasound data set and second ultrasound data set during a same pulse sequence of the array of acoustic elements.

18. The method of claim 12, wherein each event grouping of the plurality of event groupings comprises between 4 and 8 transmit-receive events.

19. The method of claim 18, wherein each ensemble of the plurality of ensembles comprises between 2 and 6 event groupings.

20. The method of claim 12, wherein determining the flow estimate comprises:
generating a first flow estimate from a first ensemble; and
generating a second flow estimate from a second ensemble, and wherein generating the B-mode image comprises generating an A-line using transmit-receive pairs associated with the first and second ensembles.

21. The method of claim 12, further comprising combining incoherently and averaging ultrasound data obtained by at least a portion of the plurality of ensembles to generate a flow A-line.

\* \* \* \* \*